United States Patent
Renz et al.

(10) Patent No.: US 7,253,288 B2
(45) Date of Patent: Aug. 7, 2007

(54) PROCESS FOR PREPARING SUBSTITUTED TETRAZOLES FROM AMINOTETRAZOLE

(75) Inventors: Robert N. Renz, Phoenix, AZ (US); Michael D. Williams, Gilbert, AZ (US); John W. Fronabarger, Phoenix, AZ (US)

(73) Assignee: Pacific Scientific Energetic Materials Company, Chandler, AZ (US)

( * ) Notice: Subject to any disclaimer, the term of this patent is extended or adjusted under 35 U.S.C. 154(b) by 0 days.

(21) Appl. No.: 11/222,434

(22) Filed: Sep. 8, 2005

(65) Prior Publication Data

US 2007/0161801 A1 Jul. 12, 2007

Related U.S. Application Data

(60) Provisional application No. 60/607,876, filed on Sep. 8, 2004.

(51) Int. Cl.
*C07D 257/06* (2006.01)
*C07D 257/04* (2006.01)
(52) U.S. Cl. ...................... 548/251; 548/250
(58) Field of Classification Search ............... 548/250, 548/251
See application file for complete search history.

(56) References Cited

U.S. PATENT DOCUMENTS

| | | | |
|---|---|---|---|
| 2,066,954 A | 1/1937 | von Herz | |
| 4,093,623 A | 6/1978 | Gilligan et al. | |
| 4,094,879 A | 6/1978 | Bates et al. | |
| 4,552,598 A | 11/1985 | Lee et al. | |
| 6,375,871 B1 | 4/2002 | Bentsen et al. | |
| 6,437,104 B1 | 8/2002 | Nickel et al. | |
| 6,469,147 B2 | 10/2002 | Nickel et al. | |
| 6,495,016 B1 | 12/2002 | Nawracala | |
| 6,648,015 B1 | 11/2003 | Chow | |
| 6,737,026 B1 | 5/2004 | Bergh et al. | |

FOREIGN PATENT DOCUMENTS

| WO | WO2001059013 | 8/2001 |
|---|---|---|
| WO | WO2003037502 | 5/2003 |

OTHER PUBLICATIONS

Fortt et al., Continuous-Flow Generation of Anhydrous Diazonium Species, Organic Process Research & Development, 2003, 762-768, vol. 7, No. 5.
Wootton et al., On-Chip Generation and Reaction of Unstable Intermediates, Lab-On-A-Chip, 2002, 4, 5-7.
Doyle et al., Alkyl Nitrite-Metal Halide Deamination Reaction. 2. Substitutive Deamination of Arylamines by Alkyl Nitrites and Cooper (II) Halides. A Direct and Remarkably Efficient Conversion of Arylamines to Aryl Halides, J. Org. Chem., 1977, 2426-2431, vol. 42, No. 14.
Tegrothenhuis et al., Normal gravity testing of a microchannel phase separator for resource utilization, NASA/CR-2001-210955 (Jun. 2001).
Brooks et al., Component development for a microchannel in situ propellant production system, 2002, AIChE 2002 Spring National Meeting held Mar. 10-14, 2002 in New Orleans, Louisiana.
Ahn et al., Centrifugal gas-liquid separation under low-gravity conditions, Separation and Purification Technology, 2000, 121-129, vol. 19, No. 1.
Günther et al., Transport and reaction in microscale segmented gas-liquid flow, Lab-On-A-Chip, 2004, 4, 278-286.
Amon et al., Direct Methanol Micro Fuel Cell for Powering Micro Sensors, http://www.darpa.mil/mto/mpg/summaries/2003_1/cmu.html (2003).
Kralj et al., Preparation of Sodium Nitrotetrazolate Using Microreactor Technology, American Institute of Aeronautics and Astronautics, 41st AIAA/ASME/SAE/ASEE Joint Propulsion Conference and Exhibit, Jul. 10-13, 2005, Tuscan, AZ.

*Primary Examiner*—Golam Shameem
*Assistant Examiner*—Karen Cheng (57) ABSTRACT

The present invention is directed to the field of substituted tetrazole synthesis and manufacture. More particularly, the present invention is directed to processes for preparing substituted tetrazoles and tetrazolate salts, such as sodium nitrotetrazolate and sodium cyanotetrazolate, using small scale and/or microreactor techniques. The use of the present techniques result in less hazardous and more efficient manufacturing processes.

9 Claims, 4 Drawing Sheets

PROCESS FOR PREPARING SUBSTITUTED TETRAZOLES FROM AMINOTETRAZOLE

CROSS-REFERENCE TO RELATED APPLICATIONS

The present application is related to and claims priority benefits from U.S. Provisional Patent Application Ser. No. 60/607,876 filed on Sep. 8, 2004, entitled PROCESS FOR PREPARING SUBSTITUTED TETRAZOLES FROM AMINOTETRAZOLE. The '876 application is hereby incorporated by reference herein in its entirety.

FIELD OF THE INVENTION

The present invention is directed to the field of substituted tetrazole synthesis and manufacture. More particularly, the present invention is directed to processes for preparing substituted tetrazoles and tetrazolate salts, such as sodium nitrotetrazolate and sodium cyanotetrazolate, using small scale and/or microreactor techniques. The use of the present techniques result in less hazardous and more efficient manufacturing processes.

BACKGROUND OF THE INVENTION

Substituted tetrazoles, and in particular tetrazolate salts substituted with nitro-, cyano-, azido- and halogens, are useful as primary explosives, as well as for other industrial applications. Conventionally, such substituted tetrazoles have been prepared through the use of cupric salts in a Sandmeyer reaction. For example, U.S. Pat. No. 4,093,623 to Gilligan et al. describes the use of Sandmeyer chemistry to prepare sodium nitrotetrazolate. In a first step, $CUSO_4$, sodium nitrite, and 5-aminotetrazole are reacted in the presence of a strong inorganic acid to form the copper acid salt of 5-nitrotetrazole. In a second step, sodium hydroxide is used to convert the acid salt to sodium 5-nitrotetrazole.

In a manufacturing setting, this synthesis is carried out as a batch process that is plagued by certain inefficiencies. Specifically, the copper acid salt of 5-nitrotetrazole which results from the first reaction step is a precipitate that must be separated from an aqueous solution of $Na_2SO_4$ and $NaNO_3$. In the second step, the precipitated copper acid salt is contacted with sodium hydroxide to form a precipitate of CuO in an aqueous solution of sodium 5-nitrotetrazole. The precipitated CuO must be separated from the aqueous solution to arrive at the final sodium nitrotetrazole product. Both of these precipitate-separation steps involve the use of filtration, which is unwieldy and inefficient in large-scale batch manufacturing processes, and which ultimately leads to increased manufacturing costs and lower overall yield of the final product due to inherent losses incurred during the additional process steps. Thus, there is a need for a method of manufacturing substituted tetrazoles that does not involve precipitation and filtration steps.

One solution is to remove the copper salts from the synthesis procedure altogether. In the case of sodium nitrotetrazole, this may be accomplished by reacting sodium nitrite directly with aminotetrazole and a strong inorganic acid (in the absence of $CuSO_4$), and then neutralizing the acidic aqueous reaction product with sodium hydroxide. This procedure leads to the formation of sodium nitrotetrazole while at the same time avoiding the precipitation of any components (and filtration steps that would accompany such precipitation). It has been found, however, that the synthesis of sodium nitrotetrazole in the absence of a metal salt can lead to the accumulation of a potentially hazardous tetrazole-diazonium intermediate, which can itself lead, through deprotonation, to the formation of an equally hazardous diazotetrazole. It is theorized that the use of cuprous salts (or other metal salts) suppresses the accumulation of the tetrazole-diazonium intermediate and thereby precludes the formation of the diazotetrazole. In any event, these intermediates and unintended by-products are extremely sensitive and, when present, can spontaneously initiate a very exothermic decomposition.

Because of the sensitive nature of these intermediates, the use of a synthesis method which omits cupric salts to manufacture sodium nitrotetrazole in a commercial batch process is not feasible. There are several reasons for this. First, exothermic decomposition of the sensitive intermediates in manufacturing-scale batch equipment could result in a large explosion which could destroy the reactor equipment and cause injury to operators. Second, even if it did not result in an explosion sufficient to destroy the equipment or cause injury to operators, the exothermic decomposition would destroy all of the starting materials in the batch as well as any final product that had already been formed. As a result of these difficulties, this method has not been considered an option for the commercial manufacture of substituted tetrazoles.

Thus, there is a need in the art for a more efficient and safer process to manufacture substituted tetrazoles and substituted tetrazole salts.

SUMMARY OF THE INVENTION

Accordingly, an object of this invention is to provide a process for preparing substituted tetrazoles and substituted tetrazole salts that is more efficient than conventional processes.

Another object of this invention is to provide a process for preparing substituted tetrazoles and substituted tetrazole salts that is safer than conventional processes.

A further object is to provide a process for preparing substituted tetrazoles and substituted tetrazole salts that is more efficient than conventional processes and yet is just as, if not more, safe than conventional processes.

Another object is to provide a process for preparing substituted tetrazoles and substituted tetrazole salts that allows for large-scale synthesis without the use of metal salts.

Yet another object is to provide a process for preparing substituted tetrazoles and substituted tetrazole salts that allows for large-scale synthesis without costly separation and filtration steps.

Another object is to provide a process for preparing substituted tetrazoles and substituted tetrazole salts that requires fewer steps than conventional processes.

Another object is to provide a process for preparing substituted tetrazoles and substituted tetrazole salts that is less expensive than conventional processes.

At least one of these objects is addressed, in whole or in part, by the present invention. The present invention is directed to a process for preparing a substituted tetrazole in a microreactor environment.

Many advantages of using microreactor technology are known and have been described in the art, but the technology has not heretofore been applied to the synthesis of substituted tetrazoles. In "Continuous-Flow Generation of Anhydrous Diazonium Species," Organic Process Research & Development 2003, 7, 762-768, Fortt et al. explain some of the advantages of using microreactor technology for reactions that involve unstable intermediates, and in particular those that involve diazonium reactive intermediates. Fortt et al. explain that, through the use of microreactor technology, dangerous reactions can be undertaken in relative safety due to the small reacting volumes involved, and precise control of various reaction conditions is possible. Fortt et al. go on to describe the application of microfluidic reactor technology to a particular reaction: the synthesis of chloroarenes through a Sandmeyer reaction. The Sandmeyer reaction used to synthesize chloroarenes involves the reaction of a benzenoid amine with an alkyl nitrite and a copper salt under anhydrous conditions (also in an organic solvent, DMF, to preclude hydroxyl-dediazonation), where a diazonium salt is formed as an intermediate. Fortt et al. describe the successful results of direct miniaturization of this Sandmeyer reaction onto a microfluidic reactor chip.

The conventional process for the preparation of a substituted tetrazole (e.g. sodium nitrotetrazolate) can also be characterized as a Sandmeyer reaction since it takes place in the presence of a copper salt, albeit under hydrated conditions and in the absence of an organic solvent. Unfortunately, the direct miniaturization solution proposed by Fortt et al. cannot be feasibly applied to the preparation of substituted tetrazoles. The reason for this is that the use of a copper salt in the conventional process results, as discussed above, in the formation of two separate copper precipitates that must be separated from the reaction system prior to further processing. Any precipitation in a microreactor system tends to rapidly clog the small-scale reactor zones and flow paths. Thus, the Fortt et al. article, while suggestive of the benefits of using microreactor technology for highly reactive systems, fails to teach a miniaturization process that can be applied to the synthesis of substituted tetrazoles.

In "On-Chip Generation and Reaction of Unstable Intermediates," Lab-On-A-Chip 2002, 2 (1), 5, Wootton et al. describe the use of microreactor technology to synthesize azo dyes, another product which results from a diazonium intermediate but which, in this instance, does not involve a Sandmeyer reaction. As with Fortt et al., Wootton et al. describe the direct miniaturization of the azo synthesis onto a microreactor chip. Notably, the azo linkages in this reaction are formed by the coupling reaction of diazonium salts, or the linkage of two aromatic constituents through a —N=N— bond. The azo dye synthesis is distinct from the present process of preparing a substituted tetrazole in that it leaves the diazonium species intact. This procedure is thus inapplicable to the preparation of substituted tetrazoles from aminotetrazole and would, in fact, be counterproductive for use in preparing such compounds.

Ultimately, Fortt et al. and Wootton et al. describe the application of microreactor technology to chemistries which are quite distinct from the tetrazole chemistry involved in the present invention. Notably, since the substituted tetrazoles of the present invention are themselves explosive in nature (hence their use in primary explosives), the unstable intermediates and by-products that may occur during their synthesis are far more dangerous than intermediates formed during the preparation of the azo dyes of Wootton et al. or the chloroarenes of Fortt et al.

While the conventional Sandmeyer process for preparing substituted tetrazoles is not suitable for direct miniaturization, it has surprisingly been discovered that substituted tetrazoles can be successfully synthesized in a microreactor in the absence of copper salts. As explained above, forming a substituted tetrazole without copper salts can lead to the unwanted accumulation of hazardous intermediates and by-products in a large scale batch process. When such synthesis is undertaken on a microreactor scale in a continuous process, however, the difficulties associated with the hazardous intermediates and by-products are minimized. Stated simply, microreactor technology can be utilized, not to improve upon the conventional method of manufacturing substituted tetrazoles, but to make possible an alternate synthesis that has up to this point been an untenable option for commercial use.

There are several ways in which the use of microreactor technology facilitates synthesis in the absence of copper salts. Increased precision of reaction control allows for a streamlined synthesis in which the reactive intermediates are quickly quenched to the final product, suppressing the accumulation of hazardous or reactive intermediates and the formation of unwanted and hazardous by-products (diazotetrazole). If the reactive intermediates do accumulate and de-stabilize, the small reaction volumes involved prevent the potentially catastrophic explosions that could occur in a batch process. In other words, destabilization would lead, at worst, to a burnt out or damaged microreactor chip and not destruction of equipment, potential harm to operators, and loss of any product already synthesized. As an added benefit of using microreactor technology, increased precision to reaction control results in better yields of the final product. Furthermore, the microreactors can be operated to produce large amounts of the desired end product by using the concept of "scale out", where multiple microreactors are run in parallel to simulate a large scale flow reactor.

Therefore, as a first aspect of the present invention, a process is provided for preparing a substituted tetrazole which involves reacting aminotetrazole, a nitrite, an acid, and a substitution compound in a reactor, where the reactor is characterized by a channel cross-sectional diameter of at most one millimeter. The substitution compound contains at least one nucleophilic species for replacing the amino group on said aminotetrazole. In one embodiment, the substitution compound is a compound containing an anion selected from, but not limited to, nitro, cyano, azido, and halogen anions. In another embodiment, the substitution compound is selected from among $NaNO_2$, NaCN, $NaN_3$, NaF, NaCl, NaBr, NaI, $KNO_2$, KCN, $KN_3$, KF, KCl, KBr, KI, $HNO_2$, HCl and HI.

As another aspect of the present invention, a process is provided for preparing a substituted tetrazole which involves reacting aminotetrazole, nitrous acid and a substitution compound in a reactor, where the reactor is characterized by a channel cross-sectional diameter of at most one millimeter.

As yet another aspect of the present invention, a process is provided for preparing a substituted tetrazole which involves a first reaction step of reacting aminotetrazole, a nitrite, an acid and a substitution compound to form a first reaction product, and then a second reaction step of reacting the first reaction product with a base, where at least the first reaction step is carried out in a reaction chamber characterized by a channel cross-sectional diameter of at most one millimeter. In one embodiment, the substitution compound is sodium nitrite. In another embodiment, the second reaction step is also carried out in a reaction chamber characterized by a channel cross-sectional diameter of at most one millimeter.

As a further aspect of the present invention, a process is provided for preparing a substituted tetrazole which involves reacting aminotetrazole, nitrous acid, and a substitution compound in a continuous process involving a series of reactors working in parallel, where each reactor is characterized by a channel cross-sectional diameter of at most one millimeter.

As yet a further aspect of the present invention, a process is provided for preparing a sodium nitrotetrazole compound which involves reacting aminotetrazole, nitric acid, and sodium nitrite in a reactor, where the reactor is characterized by a channel cross-sectional diameter of at most one millimeter. In one embodiment, sodium nitrotetrazole is prepared by reacting aminotetrazole, nitric acid, and sodium nitrite to form a first reaction product, and then reacting the first reaction product with a base to form sodium nitrotetrazole, where at least the first reaction step is carried out in a reaction chamber characterized by a channel cross-sectional diameter of at most one millimeter.

In the foregoing processes, any or all of the various reaction steps may be carried out in reaction chambers that have a channel cross-sectional diameter of less than 100 micrometers or, alternatively, less than 10 micrometers. In addition, any of the foregoing processes may be adapted to take place on a single microreactor chip. More than one such microreactor chip may be operated continuously and in series and/or in parallel to synthesize the substituted tetrazole.

BRIEF DESCRIPTION OF SEVERAL VIEWS OF THE DRAWINGS

FIG. 1 shows a manufacturing flow diagram for a process of preparing sodium nitrotetrazole.

DETAILED DESCRIPTION OF THE INVENTION

The word reactor, as used herein, refers to any chamber, space or flow path in which reactants are contacted and then a chemical reaction ensues.

The "channel cross-sectional diameter" of a reactor, as used herein, refers to the width or diameter of the reactor in the direction generally perpendicular to flow through the reactor. For reactors with irregularly-shaped cross sections, the channel cross-sectional diameter may be calculated by measuring the area of the cross section perpendicular to flow, and applying the following formula: take the square root of the cross sectional area divided by $\pi$, and multiply the product by 2.

Novel processes are provided for the preparation of substituted tetrazoles. As described, in one aspect of the invention a process is provided for preparing a substituted tetrazole which involves reacting aminotetrazole, a nitrite, an acid, and a substitution compound in a reactor, where the reactor is characterized by a channel cross-sectional diameter of at most one millimeter. While not wishing to be bound by theory, it is believed that the nitrite and the acid react to form a reactive nitrite species which reacts, in turn, with the aminotetrazole to form a tetrazole-diazonium intermediate. The tetrazole-diazonium intermediate then reacts with the substitution compound to form the desired substituted tetrazole with the evolution of nitrogen. The reactive nitrite species that forms from the reaction of the acid and the nitrite is, most commonly, nitrous acid. Thus, in another aspect of the present invention a process is provided for preparing a substituted tetrazole which involves reacting aminotetrazole, nitrous acid, and a substitution compound in a reactor, where the reactor is characterized by a channel cross-sectional diameter of at most one millimeter.

Aminotetrazole may be synthesized using known methods or may be obtained from any of a variety of known commercial sources. For example, 5-aminotetrazole may be obtained in bulk from a variety of known commercial sources. Since at least one mole of aminotetrazole will be required to form each mole of the substituted tetrazole synthesized, the quantity of aminotetrazole supplied to the reactor is dictated by the amount of end product desired.

The acid is selected from any known acid or mixtures of acids that will, when reacted with aminotetrazole, a nitrite and a substitution compound, facilitate the substitution of a nucleophilic species onto the tetrazole ring in place of the amino group. Most strong inorganic acids are suitable for use in the present invention. Non-limiting examples of suitable acids include perchloric acid, sulfuric acid, nitric acid, and halogen acids. Halogen acids include, but are not limited to, HF, HCl, HBr, and HI. Alternatively, nitric acid may be selected for use with the present invention. The acid may be supplied to the reactor in any amount that is sufficient to effect the desired substitution reaction. Alternatively, the acid may be supplied to the reactor in an amount sufficient to react with the nitrite to form enough reactive nitrite species such that substantially all of the aminotetrazole supplied to the reactor is converted to tetrazole-diazonium intermediate. Alternatively, the acid may be supplied to the reactor in a molar ratio of one or more acid equivalents per mole aminotetrazole supplied to the reactor. Optionally, the acid may be supplied to the reactor in a suitable solvent that will not interfere with the substitution reaction. The acid may, if appropriate or if desired, be supplied to the reactor under aqueous conditions.

The nitrite is selected from any known nitrite or mixtures of nitrites that will, when reacted with aminotetrazole, an acid and a substitution compound, facilitate the substitution of a nucleophilic species onto the tetrazole ring in place of the amino group. Non-limiting examples of suitable nitrites include sodium nitrite, potassium nitrite, lithium nitrite, alkali metal nitrites, alkaline earth metal nitrites, and alkyl nitrites. Alternatively, sodium nitrite may be selected for use with the present invention. The nitrite may be supplied to the reactor in any amount that is sufficient to effect the desired substitution reaction. Alternatively, the nitrite may be supplied to the reactor in an amount sufficient to react with the acid to form enough reactive nitrite species such that substantially all of the aminotetrazole supplied to the reactor is converted to tetrazole-diazonium intermediate. Alternatively, the nitrite may be supplied to the reactor in a molar ratio of at least one mole nitrite per mole aminotetrazole supplied to the reactor. Optionally, the nitrite may be supplied to the reactor in a suitable solvent that will not interfere with the substitution reaction. The nitrite may, if appropriate or if desired, be supplied to the reactor under aqueous conditions.

For the aspects of this invention in which the aminotetrazole and substitution compound are reacted with nitrous acid, in place of the acid and nitrite, the nitrous acid may be prepared by any suitable method known in the art. Alternatively, as suggested above, nitrous acid may be prepared in situ by reacting a nitrite with an acid such as perchloric acid, sulfuric acid, nitric acid, HF, HCl, HBr, or HI. Alternatively, nitrous acid may be prepared in situ by reacting sodium nitrite with an acid such as perchloric acid, sulfuric acid, nitric acid, HF, HCl, HBr, or HI. Alternatively, nitrous acid may be prepared by reacting sodium nitrite with nitric acid. Nitrous acid may be generated or supplied to the reactor in any amount that is sufficient to effect the desired substitution reaction. Alternatively, nitrous acid may be generated or supplied to the reactor in an amount sufficient to convert substantially all of the aminotetrazole supplied to the reactor to tetrazole-diazonium intermediate. Alternatively, nitrous acid may be supplied to the reactor in a molar ratio of at least one mole nitrous acid per mole aminotetrazole supplied to the reactor. Optionally, nitrous acid may be supplied to the reactor or generated in the reactor in a suitable solvent that will not interfere with the substitution reaction. The nitrous acid may, if appropriate or if desired, be supplied to the reactor or generated in the reactor under aqueous conditions.

The substitution compound is any compound that contains at least one nucleophilic species for replacing the amino group on the aminotetrazole. The nucleophilic species may be an anion. Non-limiting examples of suitable anions include $NO_2^-$, $CN^-$, $N_3^-$, and halogens. Non-limiting examples of suitable substitution compounds include $NaNO_2$, NaCN, $NaN_3$, NaF, NaCl, NaBr, NaI, $KNO_2$, KCN, $KN_3$, KF, KCl, KBr, KI, HCl, and HI. The substitution compound may be supplied to the reactor in any amount that is sufficient to prepare the desired amount of substituted tetrazole. If it is desirable to substitute an anion onto each molecule of aminotetrazole that is supplied to the reactor, the substitution compound should be supplied to the reactor in an amount such that at least one mole of the nucleophilic species is supplied per mole of aminotetrazole supplied. Optionally, the substitution compound may be supplied to the reactor in a suitable solvent that will not interfere with the substitution reaction. The substitution compound may, if appropriate or if desired, be supplied to the reactor under aqueous conditions.

In some aspects of the present invention, it is possible for a single compound to serve a dual role as both nitrite and substitution compound, or as both acid and substitution compound. For example, sodium nitrite may serve as both the nitrite (because it is a nitrite) and the substitution compound (because it contains an anion, $NO_2^-$, that can replace the amino group on the tetrazole). Likewise, hydrochloric acid may serve as both the acid (because it is a suitable acid) and the substitution compound (because it contains an anion, $Cl^-$, that can replace the amino group on the tetrazole). A person of ordinary skill in the art will recognize that when a compound serves these dual roles, it may be necessary to adjust the quantity of such compound that is supplied to the reactor. For example: if sodium nitrite is serving as both the nitrite and as the substitution compound, it may be necessary to increase the amount of sodium nitrite supplied to the reactor so that the substitution reaction can be brought to the desired or expected degree of completion.

The reaction may be carried out at any temperature that allows for and/or facilitates completion of the substitution reaction to the desired degree within desired time limits, if any. Alternatively, the reaction may be carried out in the range of about −20° C. to about 120° C. Alternatively, the reaction may be carried out in the range of about 0° C. to about 100° C., alternatively about 15° C. to about 75° C. Alternatively, the reaction may be carried out at room temperature.

The reactants described above are supplied to a reactor that is characterized by a channel cross-sectional diameter of at most one millimeter. The present invention contemplates both batch and continuous processes for the synthesis of substituted tetrazoles, but due to the small reaction volumes involved (a channel cross-sectional diameter of at most one millimeter), processes that are either wholly or partly continuous are preferred. It will be understood by those skilled in the art that, in a continuous process, the reactant amounts described above are the molar ratios in the combined reactant streams entering the reactor, as opposed to specific quantities added to a batch reactor.

Suitable reactors contemplated for use herein include virtually any reactor meeting the channel cross-sectional diameter limitation of at most one millimeter. Much has been written about miniaturized reactor systems and in particular about microreactor or microfluidic reactor technology. See, e.g., the Wootton et al. and Fortt et al. articles described above, as well as U.S. Pat. No. 6,469,147 to Nickel et al., entitled "Preparation of Azo Colorants in Microreactors"; U.S. Pat. No. 6,495,016 to Nawaracal, entitled "Microfluidic Microchip With Integrated Substance Injection"; U.S. Pat. No. 6,375,871 to Bentsen et al., entitled "Methods of Manufacturing Mircrofluidic Articles"; and U.S. Pat. No. 6,737,026 to Bergh et al., entitled "Methods for Identifying and Optimizing Materials in Microfluidic Systems." The production of microfluidic devices has been facilitated by advancements in microfabrication technology used in the electronics and semiconductor manufacturing industries. Specifically, technologies, such as photolithography, wet chemical etching, deep reactive ion etching, injection molding of plastics, and the like, have been used to fabricate microscale channels and wells in the surface of planar substrates. A second substrate is then bonded over this surface, which covers and seals the grooves and wells to form the channels and chambers. As described in U.S. Pat. No. 6,648,015 to Chow, multiple substrate layers can be bonded together and interconnected to create three dimensional microfluidic systems. Numerous materials are suitable for use as substrates, including without limitation glass, metals (such as Nickel-Chromium materials prepared using LIGA technology), and polymer materials.

Any of the technology described above can be utilized to construct reactor systems and accompanying flow paths (as well as other components) that are suitable for the present processes of preparing substituted tetrazoles. While reactors with a channel cross-sectional diameter of up to one millimeter are suitable for use herein, reactors with smaller channel cross-sectional diameters are also contemplated. The process for preparing a substituted tetrazole may be carried out in a reactor that is characterized by a channel cross-sectional diameter of at most 500 micrometers, alternatively at most 200 micrometers, alternatively at most 100 micrometers. Alternatively, the process may be carried out in a reactor that is characterized by a channel cross-sectional diameter of at most 10 micrometers, alternatively at most 1 micrometer, alternatively at most 500 nanometers, alternatively at most 100 nanometers, alternatively between 5 nanometers and 60 nanometers.

In another aspect of the present invention, the reaction of aminotetrazole, nitrite, acid, and substitution compound (or alternatively, aminotetrazole, nitrous acid, and substitution compound) is followed by a second reaction step in which the first reaction product is contacted with a base. It has been found that while a substituted tetrazole can be synthesized by the described primary reaction step, the substituted tetrazole formed by this reaction is often acidic in nature.

Thus, an additional, second reaction step is contemplated in which the reaction product of the first reaction is contacted with a base. Any known base in any amount may be used which achieves the goal of reducing or eliminating the acidity of the substituted tetrazole. Alternatively, a base may be added in sufficient quantities to bring the pH of the product of the first reaction to greater than about 6, alternatively to greater than about 7, alternatively to greater than about 8, alternatively to about 9 or greater, alternatively to about 10 or greater. A non-limiting example of one suitable base is sodium hydroxide.

Optionally, a buffer may be used with the base in the second reaction step. One purpose of using a buffer is to maintain the pH of the second reaction step in an acidic range while the reaction is ongoing, prior to eliminating the acidity (i.e. reaching a quenching point). Examples of suitable buffers include citrates, formates, succinates, acetates and propionates (e.g. sodium citrate, potassium formate, etc.).

The second reaction step may be carried out at any temperature that allows for and/or facilitates the desired pH adjustment or which achieves the goal of reducing or eliminating the acidity of the substituted tetrazole. Alternatively, the second reaction step may be carried out in the range of about –20° C. to about 120° C. Alternatively, the second reaction step may be carried out in the range of about 0° C. to about 100° C., alternatively about 15° C. to about 75° C. Alternatively, the second reaction step may be carried out at room temperature.

The base is contacted with the product of the first and primary reaction using any suitable contacting method known to the skilled artisan. For example, if a continuous process is used to react the aminotetrazole, nitrite, acid and substitution compound, the product stream of that reaction can be collected in a mixing tank. The base can then be added to the mixing tank to bring the batch to the appropriate pH level. Alternatively, the base can be added to the product stream in a continuous fashion at one or more points. In one aspect of the present invention, the step of contacting the first reaction product with a base is carried out in a reactor or reaction chamber that is characterized by a channel cross-sectional diameter of at most one millimeter. This second reaction step may also be carried out in a reactor that is characterized by a channel cross-sectional diameter of at most 500 micrometers, alternatively at most 200 micrometers, alternatively at most 100 micrometers. Alternatively, this second reaction step may be carried out in a reactor that is characterized by a channel cross-sectional diameter of at most 10 micrometers, alternatively at most 1 micrometer, alternatively at most 500 nanometers, alternatively at most 100 nanometers, alternatively between 5 nanometers and 60 nanometers.

In one embodiment of the present invention, the first and second reaction steps are carried out in continuous fashion on a single microfluidic reactor chip. It is contemplated that more than one such chip may be operated in parallel to "scale-out" the manufacture of the substituted tetrazole to commercial quantities. In an alternative embodiment, only the first reaction step is carried out in parallel on more than one microfluidic reactor chip. The product streams of the multiple microfluidic reactor chips are combined into a single product stream, which is contacted with a base in a larger reaction chamber that may be characterized by a channel cross-sectional diameter of greater than one millimeter. The skilled artisan will understand that other combinations involving scale out and alternative contacting modes for the base can be applied to the present invention.

Several embodiments of the present invention will now be described with particular application to a process for preparing sodium nitrotetrazole. These embodiments are exemplary in nature, and are not intended to limit the invention described herein.

Figure 1:
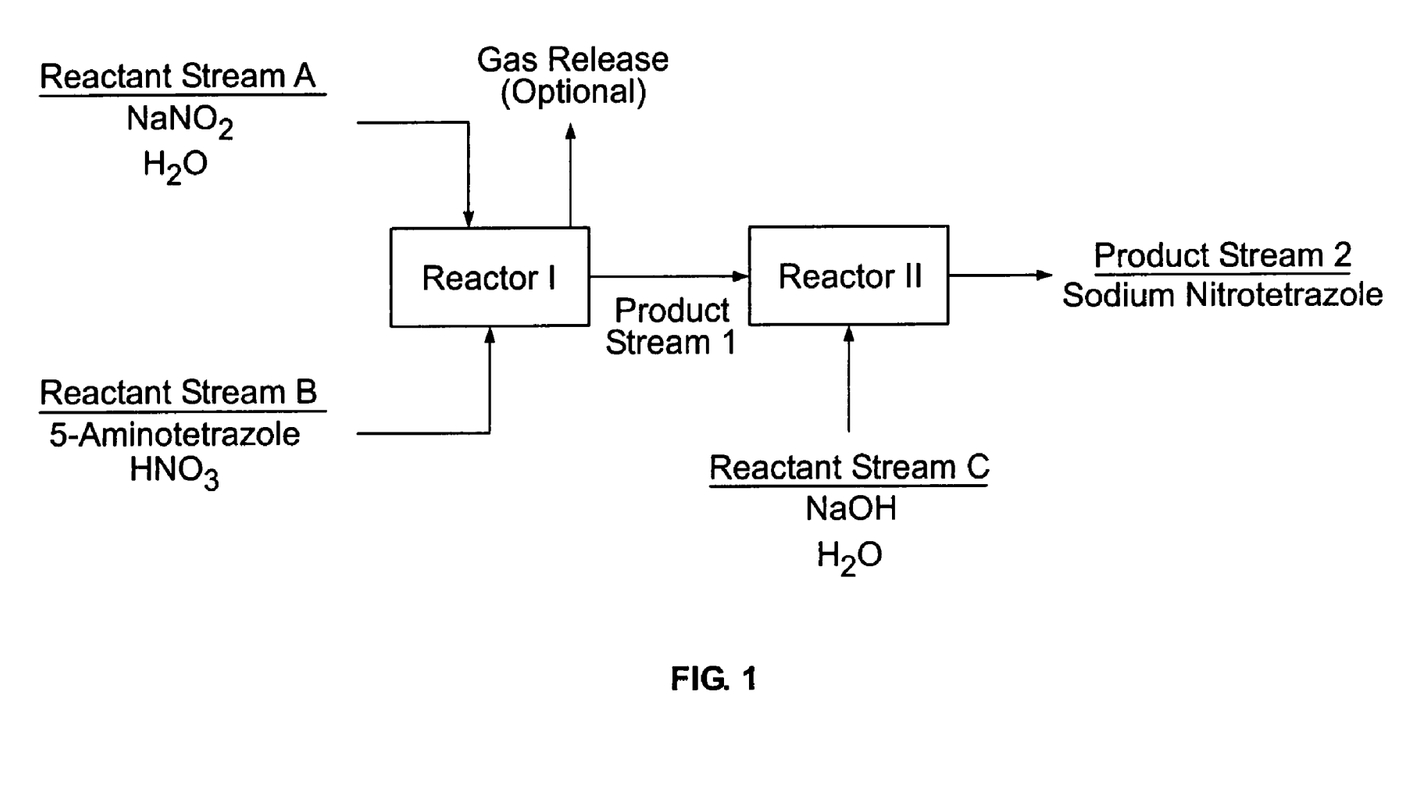
FIG. 1 shows a manufacturing flow diagram for the present process of preparing a substituted tetrazole. In particular.

A manufacturing flow diagram for the inventive process of preparing sodium nitrotetrazolate is depicted in FIG. 1. As is shown, two reactant streams enter Reactor I. Reactant Stream A consists of an aqueous sodium nitrite solution. Reactant Stream B consists of 5-aminotetrazole and an aqueous nitric acid solution. Gases that are generated during the reaction of Reactant Streams A and B (most likely $N_2$ and $NO_x$) may optionally be released. The remaining liquid product (Product Stream 1) is sent to Reactor II. Product Stream 1 is comprised primarily of the free acid of nitrotetrazole. In Reactor II, the free acid of nitrotetrazole is contacted with Reactant Stream C, which consists of an aqueous solution of sodium hydroxide (a buffer may optionally be used at this point, to maintain the reaction at acidic levels until quenching). The basic sodium hydroxide solution raises the pH of Product Stream 1 to non-acidic levels (if a buffer is present, the pH may be raised to non-acidic levels by, for example, adding non-buffered sodium hydroxide to the stream at a separate point). Product Stream 2, which consists of the desired sodium nitrotetrazolate product, exits from Reactor II and is collected. In the inventive process, Reactor I and optionally Reactor II are characterized by a channel cross-sectional diameter of at most one millimeter. To facilitate the reactions, Reactor I and/or Reactor II may be heated or cooled, or portions of either reactor may be heated or cooled. Product Stream I may also be heated or cooled.

Figure 2:
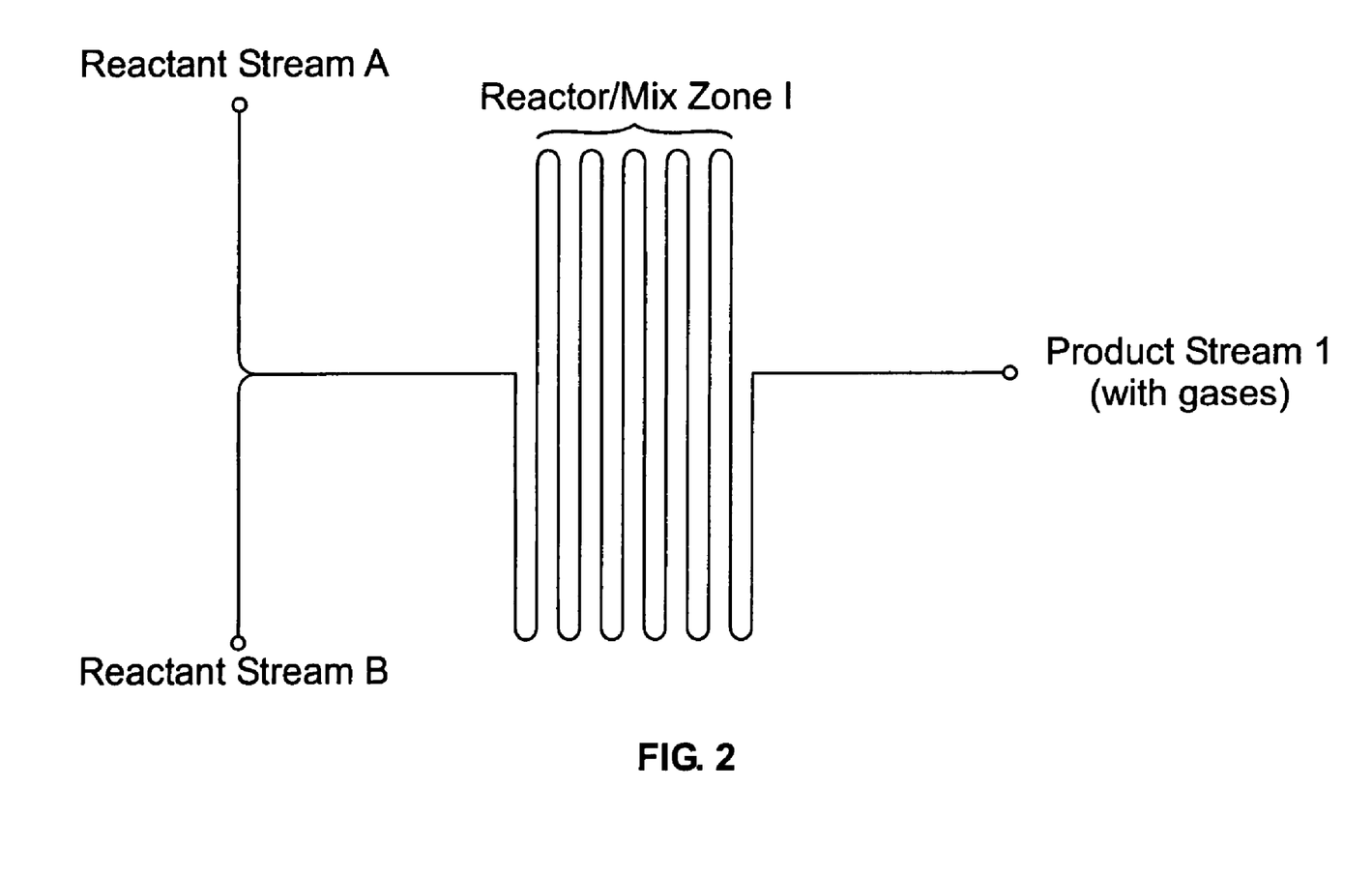
FIG. 2 shows a schematic of a microfluidic reactor chip channel pattern for use with a portion of the process depicted in FIG. 1.

The manufacturing process depicted in FIG. 1 may be carried out, either in whole or in part, on a microfluidic reactor chip manufactured by methods known in the art, some of which are discussed above. FIG. 2 depicts a microfluidic reactor chip channel pattern for use with the first portion of the manufacturing process depicted in FIG. 1. As is shown, Reactant Stream A and Reactant Stream B are combined in a microfluidic channel and fed to the serpentine Reactor/Mix Zone I on the chip. Reactant Streams A and B react in Reactor/Mix Zone I to form the acidic sodium nitrotetrazole and by-product gases, all of which exits the chip as Product Stream 1. Reactor/Mix Zone I may optionally be heated or cooled by any means known to those skilled in the art, such as through the use of localized heaters or coolers affixed or applied to the surface of the microreactor chip. As another option, a first portion of Reactor/Mix Zone I is heated, and a second portion of Reactor/Mix Zone I is cooled. In one embodiment, Product Stream 1 (and, optionally, product streams from other microfluidic reactor chips operating in parallel) is sent to a batch mixer. The gases from Product Stream 1 are vented out of the top of the batch mixer, while the liquid product is contacted with sodium hydroxide to complete the formation of non-acidic sodium nitrotetrazole.

Figure 3:
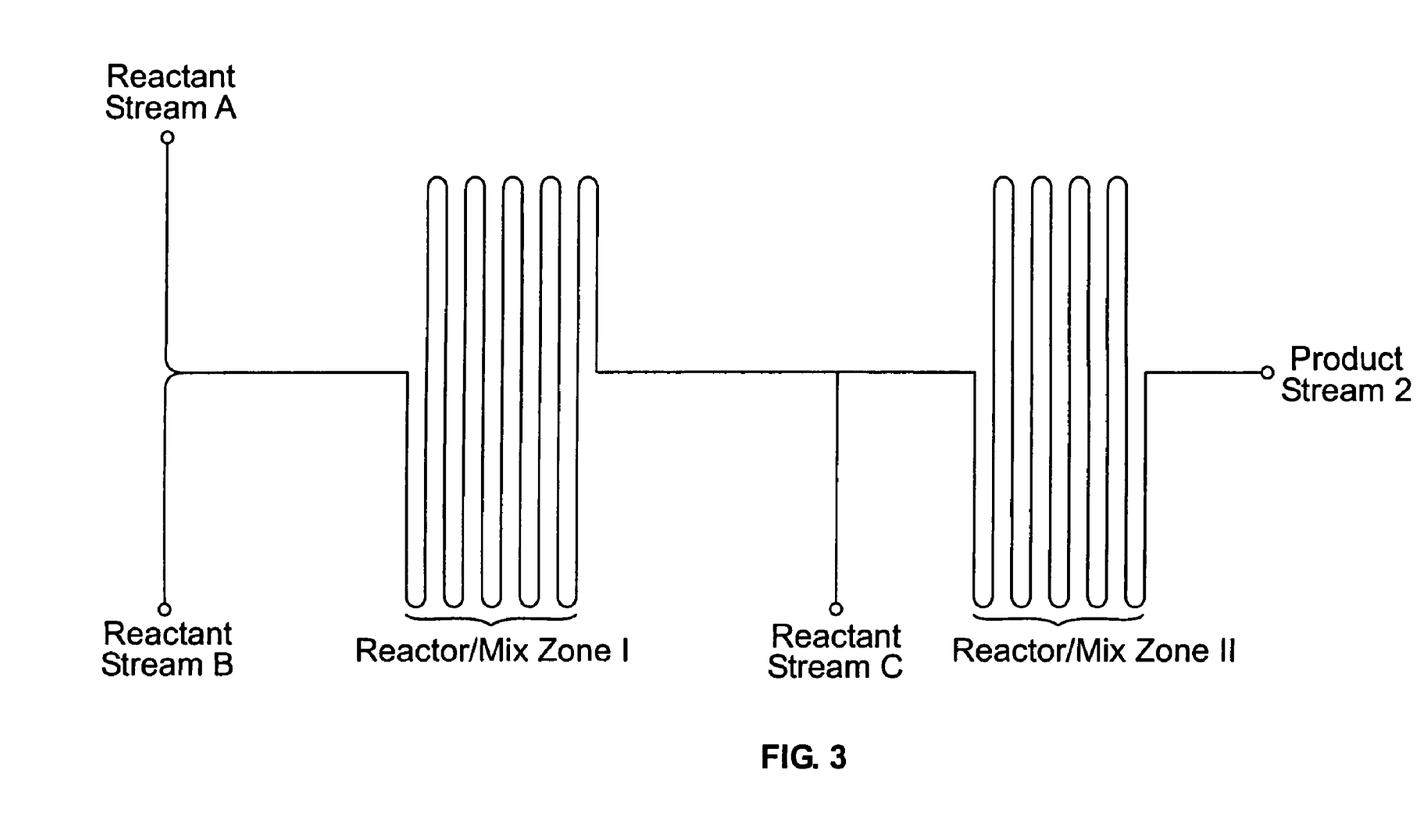
FIG. 3 shows a schematic of a microfluidic reactor chip channel pattern for use with the entire process depicted in FIG. 1.

FIG. 3 depicts a microfluidic reactor chip channel pattern for use with the entire manufacturing process depicted in FIG. 1. As is shown, Reactant Stream A and Reactant Stream B are combined in a microfluidic channel and fed to the serpentine Reactor/Mix Zone I on the chip. Reactor/Mix Zone I may optionally be heated and/or cooled as described above. Reactant Streams A and B react in Reactor/Mix Zone I to form the acidic sodium nitrotetrazole and by-product gases. Upon leaving Reactor/Mix Zone I, the reaction product may optionally be fed to a gas-liquid microseparator (not depicted in FIG. 3), which separates the gases generated during the first reaction step from the liquid product. Any suitable microseparator known to those skilled in the art of microreactor technology may be employed in this portion of the chip. Several non-limiting examples of microseparators that could be adapted for use with the present invention are described in U.S. Pat. No. 6,737,026 to Bergh et al., entitled "Methods for identifying and optimizing materials in microfluidic systems"; Ward et al., "Normal gravity testing of a microchannel phase separator for resource utilization," NASA/CR-2001-210955 (June 2001) (publication available from the NASA Center for Aerospace Information); Brooks et al., "Component development for a microchannel in situ propellant production system" (paper prepared for presentation at the AIChE 2002 Spring National Meeting held Mar. 10-14, 2002 in New Orleans, La.); Ahn et al., "Centrifugal gas-liquid separation under low-gravity conditions," Separation and Purification Technology, Vol. 19, No. 1, at 121; Gunther et al., "Transport and reaction in microscale segmented gas-liquid flow," Lab-On-A-Chip 2004, 4, at 282; and at the following website: http://www.darpa.mil/mto/mpg/summaries/2003_1/cmu.html (fuel cell technology in which $CO_2$ gas is separated from a liquid stream with the use of selective membranes).

Optionally, the reaction product leaving Reactor/Mix Zone I may be cooled to room temperature prior to entering the gas-liquid microseparator. This cooling may be accomplished by any means known to those skilled in the art, such as passing cooled gas streams over a portion of the microreactor chip.

With reference to FIG. 3, the liquid product stream which exits Reactor/Mix Zone I (or the stream which exits the optional gas-liquid microseparator) is combined with Reactant Stream C in a microfluidic channel which is fed into Reactor/Mix Zone II. Reactor/Mix Zone II may optionally be heated and/or cooled as described above. The desired sodium nitrotetrazole product exits the chip as Product Stream 2.

It has been found that the application of the processes described herein (including the general and specific embodiments that have been described) achieves the goals of providing a process for the preparation of substituted tetrazoles that is both safe and more efficient than conventional processes, does not require the use of copper salts, is less expensive than conventional processes, and is suitable for use in large-scale manufacturing operations.

Those skilled in the art will appreciate that the specifics of the processes outlined above may be modified, without departing from the present disclosure.

EXAMPLES

The following examples demonstrate the use of the present processes to prepare substituted tetrazoles in a manner which is more efficient and less hazardous than conventional processes.

Example 1

The following experiment demonstrates the feasibility of preparing sodium nitrotetrazolate on a small scale in the absence of copper salts.

First, 0.20 g $NaNO_2$ was dissolved in 5 ml water and cooled in an ice bath to approximately 2° C. Next, 0.10 g 5-aminotetrazole was dissolved in 5 ml of a 1:10 $HNO_3/H_2O$ solution. The 5-aminotetrazole solution was then added dropwise to the $NaNO_2$ solution (which was still being cooled in the ice bath) over a period of about 8 minutes. Effervescence was observed, and the temperature increased from 2° C. to 4-5° C. and then back to 2° C. after 15 minutes.

The reaction product was removed from the ice bath. A solution of 2.0 g NaOH in 20 ml $H_2O$ was added to the reaction product dropwise until the mixture reached a pH of about 11.2. Upon addition of the NaOH solution, the reaction mixture turned from clear to yellow and effervesced. The resulting solution was stripped on a rotovap to about 5 ml and cooled to induce crystallization.

The resulting yellow crystalline product was washed with $H_2O$ and then subjected to infrared and differential scanning calorimetry analysis. The results of these two analyses indicate that the product is sodium nitrotetrazolate.

This example establishes the feasibility of preparing sodium nitrotetrazolate on a small scale and in the absence of copper salts. Notably, sodium nitrotetrazolate was formed without the use of any precipitate-forming intermediate steps.

Example 2

A glass microchip (50 mm×50 mm) is made using direct-write laser lithography, wet chemical etching and bonding techniques. As part of the preparation process, channels are etched into the glass substrate using a buffered oxide etching solution ($HF/NH_4F$). External access holes are drilled, and the channels are enclosed by bonding a glass cover plate to the etched surface. The etched channels have an average depth of 100 micrometers and an average width of 100 micrometers. The reactor channel pattern is schematically described in FIG. 2.

A 0.6 M aqueous solution of $NaNO_2$ is prepared for Reactant Stream A. A solution is prepared for Reactant Stream B by dissolving 10 g of 5-aminotetrazole in 500 ml of a 1:10 v/v ratio $HNO_3/H_2O$ solution.

Using an IVEK positive displacement pump, the $NaNO_2$ solution is introduced into the Reactant Stream A inlet at a flow rate of 3.2 microliters per minute, and the aminotetrazole solution is introduced into the Reactant Stream B inlet at a flow rate of 3.2 microliters per minute. Reactor/Mix Zone I is cooled to 5° C. by contacting the microfluidic reactor to a cooled metal block.

The reaction product leaving the Product Stream 1 outlet of the microchip is collected in a 50 ml Erlenmeyer flask. The gaseous portion of the reaction product is vented out the top of the flask. The reactor is left to run for 4 days, resulting in approximately 20 ml of liquid reaction product in the flask.

The reactor is halted and the flask is removed from the apparatus. A stir bar is placed into the flask, and a NaOH solution is added dropwise until the pH of the mixture in the flask is about 11.

The resulting solution is partially stripped on a rotovap and then cooled to crystallization. The resulting crystalline product was washed with $H_2O$ and then subjected to infrared and differential scanning calorimetry analysis. The results of these two analyses indicate that the product is sodium nitrotetrazolate.

Example 3

Figure 4:
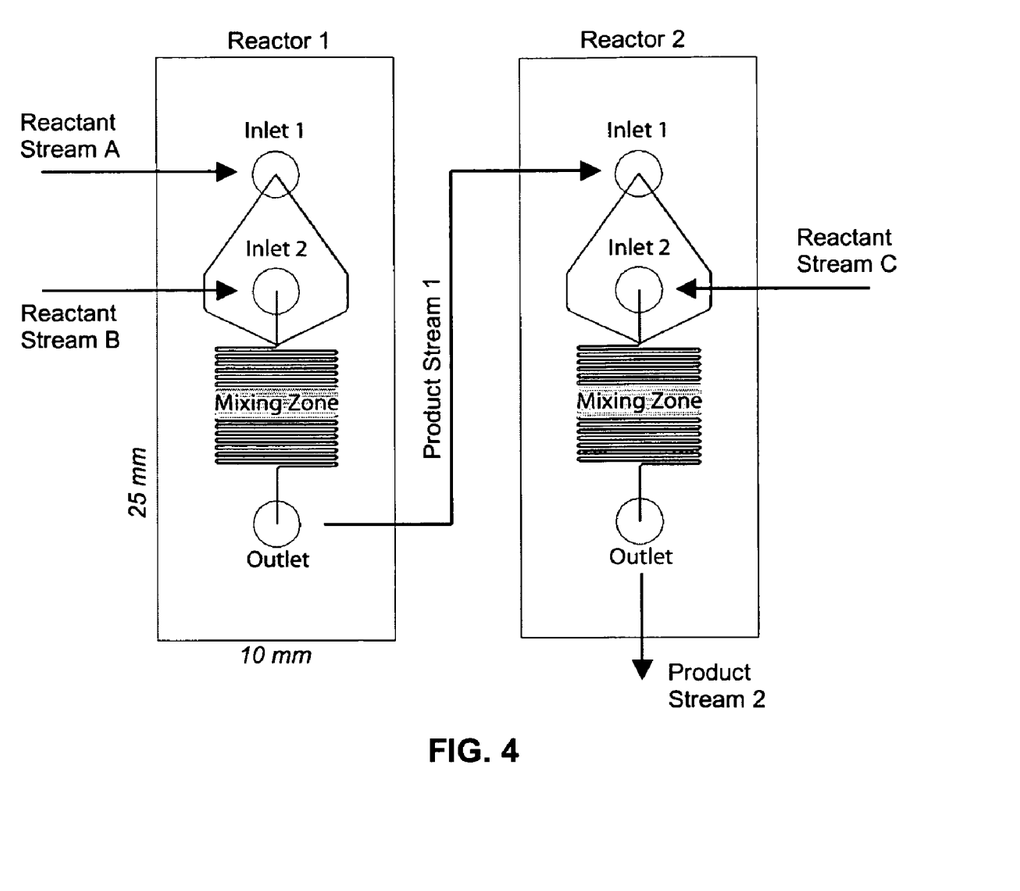
FIG. 4 shows two microfluidic reactor chips used in series to prepare sodium nitrotetrazole.

Silicon microchips (10 mm×25 mm) were constructed using standard lithography processes, wet chemical etching and bonding techniques. As part of the preparation process, channels were etched into the silicon substrate using a buffered oxide etching solution ($HF/NH_4F$). External access holes were drilled, and the channels were enclosed by anodic bonding of a pyrex cover plate to the silicon surface. The etched channels have an average depth of 50 micrometers and an average with of 160 micrometers. The silicon microfluidic reactor chips (with reactor channel patterns) are shown in FIG. 4.

A 0.2 M aqueous $NaNO_2$ solution was prepared for Reactant Stream A. A combined aqueous solution of 0.05 M 5-aminotetrazole and 1.5 M sulfuric acid was prepared for Reactant Stream B.

Using a Harvard multi-syringe pump, each reactant stream was fed to a first reactor (labeled as "Reactor 1" in FIG. 4) at a rate of 25 microliters/minute (a 1:1 v/v ratio). Referring to FIG. 4, Reactant Stream A was fed to Inlet 1 of Reactor 1, and Reactant Stream B was fed to Inlet 2 of Reactor 1. During the reaction, Reactor 1 was maintained at 20° C. by submerging the microfluidic reactor in a cold water bath.

Again referring to FIG. 4, the reaction product leaving the outlet of Reactor 1 ("Product Stream 1") flowed through cooled PTFE tubing (500 μm×31 cm, 62 μL volume) to Inlet 1 of Reactor 2. An aqueous solution of 0.4 M citrate and 2 M NaOH was prepared for Reactant Stream C. Reactant Stream C was fed to Inlet 2 of Reactor 2 at a rate of 50 microliters/minute (a 1:1 v/v ratio with Product Stream 1, which resulted in the stream having a pH of about 4.5). Reactor 2 was maintained at 10° C. by submerging the microfluidic reactor in a cold water bath.

The product leaving the outlet of Reactor 2 ("Product Stream 2") flowed through 1.1 meters of 0.02" ID PTFE tubing and was then quenched by addition of a 4. M aqueous NaOH solution, via a T junction (not shown in FIG. 4), at a volumetric flow rate equal to the flow rate of the product from Reactor 2. The presence of sodium nitrotetrazolate in the resulting product stream was confirmed with the use of high pressure liquid chromatography.

More than one set of such reactor chips may be operated in parallel to "scale-out" the manufacture of the sodium nitrotetrazolate to larger quantities.

All patents, test procedures, and other documents cited herein are fully incorporated by reference to the extent such disclosure is not inconsistent with this invention and for all jurisdictions in which such incorporation is permitted.

While the present invention has been described and illustrated by reference to particular embodiments, it will be appreciated by those of ordinary skill in the art that the invention lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

What is claimed is:

1. A process for preparing a substituted tetrazole, comprising:
    (a) providing aminotetrazole;
    (b) providing nitrous acid;
    (c) providing a substitution compound, wherein said substitution compound contains a nucleophilic species for replacing the amino group on said aminotetrazole, wherein said nucleophilic species is an anion selected from the group consisting of $NO_2^-$, $CN^-$, azido, and halogen anions; and
    (d) reacting said aminotetrazole, said nitrous acid, and said substitution compound under conditions suitable to form a substituted tetrazole;
    wherein the reaction is carried out in a reaction chamber that has a channel cross-sectional diameter of less than one millimeter; and
    wherein the reaction is carried out in the absence of copper precipitates.

2. The process of claim 1, wherein said substitution compound is selected from the group consisting of $NaNO_2$, NaCN, $NaN_3$, NaF, NaCl, NaBr, NaI, $KNO_2$, KCN, $KN_3$, KF, KCl, KBr, KI, $HNO_2$, HCl, and HI.

3. The process of claim 1, wherein the reaction is carried out in a reaction chamber that has a channel cross-sectional diameter of less than 100 micrometers.

4. The process of claim 1, further comprising the steps of:
    (e) providing a base; and
    (f) contacting said base with the reaction product of said aminotetrazole, said nitrous acid, and said substitution compound.

5. The process of claim 4, wherein said base is sodium hydroxide.

6. The process of claim 4, wherein said contacting step is carried out in a reaction chamber that has a channel cross-sectional diameter of less than one millimeter.

7. The process of claim 6, wherein said process takes place on a single microfluidic reactor chip.

8. A process for manufacturing a substituted tetrazole, wherein the process of claim 7 is carried out in a continuous fashion on said chip.

9. A process for manufacturing a substituted tetrazole, wherein the process of claim 8 is carried out in continuous fashion on more than one said chip operating in parallel.

* * * * *